United States Patent [19]

Drent et al.

[11] Patent Number: 4,731,467

[45] Date of Patent: Mar. 15, 1988

[54] PROCESS FOR THE PREPARATION OF A DIESTER OF A 2-BUTENEDIOIC ACID

[75] Inventors: Eit Drent; Antonius J. M. Breed, both of Amsterdam, Netherlands

[73] Assignee: Shell Oil Company, Houston, Tex.

[21] Appl. No.: 2,489

[22] Filed: Jan. 12, 1987

[30] Foreign Application Priority Data

Jan. 29, 1986 [GB] United Kingdom ................. 8602178

[51] Int. Cl.$^4$ ............................................. C07C 67/38
[52] U.S. Cl. .................................... 560/204; 502/102; 502/155; 502/222; 502/223; 502/325; 502/326; 560/193; 562/595
[58] Field of Search ................ 560/204, 193; 562/595; 502/102, 155, 222, 223, 325, 326

[56] References Cited

U.S. PATENT DOCUMENTS

| 3,076,032 | 1/1963 | Riemenschneider et al. | 560/204 |
|---|---|---|---|
| 3,530,168 | 9/1970 | Biale | 560/204 |
| 3,755,419 | 8/1973 | Fujii et al. | 560/204 |
| 3,759,984 | 9/1973 | Fujii et al. | 560/204 |
| 4,281,174 | 9/1981 | Current | 560/204 |
| 4,379,939 | 4/1983 | Radel et al. | 560/193 |

Primary Examiner—Werren B. Lone
Assistant Examiner—Vera C. Clarke

[57] ABSTRACT

Process for the preparation of diesters of 2-butenedioic acids by reacting an optionally substituted acetylenically unsaturated hydrocarbon having two carbon atoms less than said 2-butenedioic acid, carbon monoxide, a quinone in the presence of a of Group VIII noble metal or a compound thereof, and optionally, a redox agent.

30 Claims, No Drawings

PROCESS FOR THE PREPARATION OF A DIESTER OF A 2-BUTENEDIOIC ACID

FIELD OF THE INVENTION

The invention relates to a process for the preparation of a diester of a 2-butanedioic acid, 2-butenedioic acids, particularly the cis configuration maleic acid.

BACKGROUND OF THE INVENTION

It is known from U.S. Pat. No. 3,755,419 to prepare 2-butenedioic acid or a derivative thereof by reacting acetylene with carbon monoxide and an alcohol in the presence of a palladium compound having a strong acid residual group, an amino acid and a heavy metal salt. The examples of this known process show that the 2-butenedioate esters were obtained in a low yield, calculated on starting acetylene. Moreover, an appreciable part of the esters formed consisted of the trans configuration, dimethyl fumarate.

It is an object of the present invention to prepare diesters of 2-butenedioic acids in a very high yield. Another object of the present invention is to obtain such diesters for a very large part in the cis-configuration.

SUMMARY OF THE INVENTION

This invention provides a process for the preparation of a diester of a 2-butenedioic acid which process comprises reacting an optionally substituted acetylenically unsaturated hydrocarbon having two carbon atoms per molecule less than said 2-butenedioic acid, carbon monoxide, an alcohol and a quinone in the presence of a noble metal selected from the group consisting of Group VIII of the Periodic Table of the Elements and compounds thereof.

DESCRIPTION OF THE PREFERRED EMBODIMENTS

The noble metals which are used in the process according to the present invention are platinum, rhodium, ruthenium, palladium iridium and/or osmium. These metals may be used in metallic form or as compounds. Mixtures of compounds of the same or different such noble metals or mixtures of such noble metals in metallic form may be used. The noble metals may be used as finely divided metals, not supported on a carrier, or supported on a carrier such as, for example, activated carbon, pumice or graphite. The present process is preferably carried out in the presence of palladium and/or a compound of palladium. Very good results have been obtained with compounds of palladium. Examples of suitable compounds of Group VIII noble metals are salts, such as nitrates, sulfates, halides, (fluorides, chlorides, bromides and iodides) and carboxylates. Among the carboxylates, salts of alkanoic acids having not more than 12 carbon atoms per molecule are preferred, particularly the Pd (II) salts. Palladium(II) acetate is most preferred.

Further examples of suitable palladium compounds are palladium complexes such as bis(2,4-pentanedionato)palladium, bis(picolinato)palladium, tetrakis(triphenylphosphine)palladium, tris(dibenzyldeneacetone)dipalladium, bis(triphenylphosphine)(1,4-benzoquinone)palladium, tetrakisacetonitrilepalladium tetrafluoroborate, bis(tri-o-tolylphosphine)palladium acetate, bis(triphenylphosphine)palladium sulfate, palladium olefin complexes, for instance di-$\mu$-chloro-dichlorobis(ethylene)dipalladium([Pd.C$_2$H$_4$.Cl$_2$]$_2$), and di-$\mu$-chloro-dichlorobis(propylene)dipalladium([Pd.C$_3$H$_6$.Cl$_2$]$_2$), and palladiumhydride complexes. Palladium may be used in complex combination with phosphites, such as triphenyl phosphite or tributyl phosphite, or in complex combination with 1,2-di(dimethylphosphino)ethane or 1,2-di(diphenylphosphino)ethane.

The quinone applied in the process according to the present invention may be an ortho-quinone or a para-quinone and can be, for example, a benzoquinone, a napthoquinone, an anthraquinone or a chrysenequinone. Preference is given to optionally substituted benzoquinones, particularly to p-benzoquinones. According to a preferred embodiment of the present invention, halogen-substituted p-benzoquinones are present with very high yields of diesters of dicarboxylic acids being obtained. In this embodiment, one or more fluorine, chlorine, bromine and/or iodine atoms are attached to the aromatic nucleus of the p-benzoquinone. Examples of such quinones are 2-iodo-, 2-bromo-, 2-chloro- and 2-fluoro-benzoquinone, 2,6-diiodo-, 2,6-dibromo-, 2,6-dichloro- and 2,6-difluoro-p-benzoquinone, 2,3,6-triiodo-, 2,3,6-tribromo-, 2,3,6-trichloro- and 2,3,6-trifluoro-p-benzoquinone. Tetrahalo-p-benzoquinones are preferred, particularly tetrachloro-p-benzoquinone (also referred to as "chloranil"). According to another preferred embodiment unsubstituted p-benzoquinone is applied in the present process. Further examples of suitable quinones are 9,10-anthraquinone, 1,4-naphthoquinone, 5,6-chrysenequinone and alkyl-substituted p-benzoquinones such as 2-methyl-p-benzoquinone and 2,6-dimethyl-p-benzoquinone. Mixtures of quinones, for example, of p-benzoquinone and a halogen-substituted p-benzoquinone may be present.

It has, moreover, been found that the yield of diesters of 2-butenedioic acids is further enhanced by carrying out the present process in the presence of a redox agent comprising a copper, iron, vanadium, cobalt or manganese salt of methanesulfonic acid, a substituted methanesulfonic acid, sulfuric acid or perchloric acid. Mixtures of such salts may be used, for example of copper and iron salts. Among the substituted methanesulfonates, preference is given to halomethanesulfonates of said metals, i.e. mono-, di- and trihalomethanesulfonates, "halo" referring to fluoro, chloro, bromo or iodo. Preference is given to trifluoromethanesulfonates, particularly to cupric trifluoromethanesulfonate. Other examples of substituents on on methanesulfonates are methyl, ethyl, propyl and isopropyl groups. Cupric and ferrous perchlorate are two other preferred redox agents.

The process according to the present invention may be carried out using a molar ratio noble metal of Group VIII and/or a compound thereof to optionally substituted acetylenically unsaturated hydrocarbon which is not critical and may vary within wide ranges. This molar ratio is suitably in the range of from $10^{-2}$ to $10^{-6}$.

The process according to the present invention may be carried out using a molar ratio redox agent to noble metal of Group VIII and/or a compound thereof which is not critical and may vary within wide ranges. This molar ratio is suitably in the range of from 0.5 to 1000 and preferably from 1 to 200.

The process according to the present invention results in the formation of a diester of a 2-butenedioic acid and of a hydroquinone. The hydroquinone may be recovered from the reaction mixture and, if desired, purified. The isolated and optionally purified hydroquinone may be used for any suitable purpose but is prefeɪ bly oxidized in a suitable manner to the corresponding quinone which quinone is preferably used in the process according to the present invention.

The process according to the present invention can be carried out using a molar ratio quinone to optionally substituted acetylenically unsaturated hydrocarbon which is not critical and which may vary within wide limits. This molar ratio may vary, for example, in the range of from 0.5:1 to 10:1.

The process according to the present invention can be carried out using a molar ratio carbon monoxide to optionally substituted acetylenically unsaturated hydrocarbon which is not critical and may vary within wide limits, preferably in the range of from 0.5:1 to 20:1 and particularly from 1:1 to 10:1, the stoichiometric ratio being 2.

The process according to the present invention can be carried out in wide ranges of temperature and pressure, preferably in the range of from 20° C. to 200° C., more preferably from 50° C. to 125° C., and at a pressure preferably in the range of from 5 to 200 bar, more preferably from 10 to 100 bar.

The alcohol can be applied in a molar ratio alcohol to optionally substituted acetylenically unsaturated hydrocarbon which is not critical and may vary within wide limits. This molar ratio is suitably at least the stoichiometric molar ratio which is 2 and may be, if desired, in the range of from 2 to 1000.

The process according to the present invention can be carried out in the absence of or, which is preferred, in the presence of a solvent which does not inhibit the reaction. The alcohol which is used as a reactant may be used as a solvent. Very good results have been obtained with ethers. Examples of ethers are methyl ethyl ether, diethyl ether, dipropyl ether, tetrahydrofuran, dimethyl ether of diethylene glycol (also referred to as "diglyme"), methyl tert-butyl ether, dichloroethyl ether, ethyl phenyl ether, diethylene glycol diethyl ether and 1,4-dioxane. Other examples of suitable solvents are halogenated hydrocarbons such as chloroform, chlorobenzene, carbon tetrachloride and perfluoroalkanes; esters such as the methyl and ethyl esters of formic acid, acetic acid, adipic acid, succinic acid, propionic acid, oxalic acid and benzoic acid; sulfones such as dimethyl sulfone, methyl butyl sulfone and tetrahydrothiophone 1,1-dioxide (also referred to as "sulfolane"); aromatic hydrocarbons such as benzene, toluene and the three xylenes; cycloalkanes such as cyclohexane; and nitrobenzene.

The process according to the present invention is suitably carried out with an optionally substituted acetylenically unsaturated hydrocarbon carrying a hydrogen atom to at least one of the triple-bonded carbon atoms. Preference is given to optionally substituted alkynes having in the range of from 2 to 20 and particularly 2 to 10 carbon atoms per molecule. Very good results have been obtained with ethyne, also referred to as "acetylene". Other examples of suitable acetylenically unsaturated hydrocarbons are propyne, 1-butyne, 2-butyne, 1-pentyne, 2-pentyne, the n-hexynes, the n-heptynes, the n-octynes, the n-nonynes, the n-decynes, the n-undecynes, the n-dodecynes, the n-eicosynes, 3-methyl-1-butyne, 3-methyl-1-pentyne, 2-ethyl-3-hexyne, 3-ethyl-1-octyne, phenylethyne, benzylethyne and cyclohexylethyne.

A wide variety of alcohols may be used in the process according to the present invention. The alcohol may be mono- or polyhydric, primary, secondary or tertiary, or aliphatic cycloaliphatic or aromatic. Monohydric alcohols having in the range of from 1 to 20 carbon atoms per molecule and, particularly, alkanols, are preferred. Very good results have been obtained with methanol. Other examples of suitable alcohols are ethanol, propanol, butanol, pentanol, hexanol, heptanol, oxtanol, nonanol, decanol, ethylene glycol, diethylene glycol, propylene glycol, ethylene glycol monoalkyl ethers (the alkyl group having up to, for example, 10 carbon atoms), 1,3-butanediol, cyclohexanol, phenol, benzyl alcohol, 2-naphthol and 2-phenanthrol.

The acid portion of the diester obtaind according to the present invention is derived from the optionally substituted acetylenically unsaturated hydrocarbon and the alcohol portion of the diester is derived from the alcohol. Accordingly, ethyne, methanol and carbon monoxide are converted into dimethyl maleate and dimethyl fumarate; propyne, ethanol and carbon monoxide into diethyl 2-methyl-2-butenedioate; 1-butyne, methanol and carbon monoxide into dimethyl 2-ethyl-2-butenedioate.

The process according to the invention can be carried out batchwise, semi-continuously or continuously. The reaction time varies in relation to the temperature used and is usually between 0.5 to 20 hours.

The following examples are intended to illustrate the invention and are not to be construed as a limitation thereof.

EXAMPLES 1-6

The Examples 1-6 were carried out in a 300 ml autoclave made of Hastelloy C ("Hastelloy" is a trade name) provided with a magnetically driven stirrer. In all experiments the autoclave was charged with palladium(II) acetate (0.1 mmol), methanol (10 ml, 247 mmol) and diglyme (40 ml). The autoclave was further charged with a quinone and a redox agent (except in Example 2), as detailed in the Table hereinafter, flushed with carbon monoxide, charged with carbon monoxide until a partial pressure thereof of 15 bar was obtained and charged with acetylene until a partial pressure thereof of 2.4 bar was obtained, which is equivalent to about 35 mmol of acetylene. Then, the autoclave was heated to the temperature stated in the table and kept at this temperature for the time stated in the table. At the end of this period, the amounts of dimethyl maleate, dimethyl fumarate and dimethyl 2,4-hexadienoate were determined mass spectrometrically; from these amounts the yields calculated on acetylene, presented in the table were determined. Traces of methyl 3-methoxyacrylate and of methyl propynoate were observed in the Examples 1-5.

Comparison of Examples 1 and 2 shows that the presence of cupric perchlorate enhances the yield of dimethyl maleate.

Comparison of Examples 1 and 3 shows that the presence of chloranil allows a higher yield of dimethyl maleate than the presence of p-benzoquinone.

Comparison of Example 2 with Examples 4 and 5 shows that the presence of ferrous perchlorate and vanadyl sulfate, respectively, enhances the yield of dimethyl maleate.

In Example 6, methyl 3-methoxyacrylate was formed in a yield of 40%.

TABLE

| Example | Quinone mmol | Redox agent mmol | Reaction time, h | Reaction temp., °C. | Yield, %, of dimethyl maleate | Yield, %, of dimethyl fumarate | Yield, %, of dimethyl 2,4-hexadienoate |
|---|---|---|---|---|---|---|---|
| 1 | chloranil 50 | cupric perchlorate 2 | 1 | 65 | 55 | 2 | 11 |
| 2 | chloranil 50 | none | 5 | 80 | 35 | 12 | 0 |
| 3 | p-benzoquinone 50 | cupric perchlorate 2 | 1 | 65 | 37 | 1.4 | 11 |
| 4 | chloranil 50 | ferrous perchlorate 4 | 5 | 80 | 77 | 9 | 0 |
| 5 | chloranil 50 | vanadyl sulphate 2 | 5 | 80 | 71 | 13 | 6 |
| 6 | chloranil 50 | cupric trifluoro-methanesulphonate 2 | 1 | 90 | 45 | 3 | 2 |

COMPARATIVE EXPERIMENT A

An experiment was carried out which differed from Example 2 only in that cupric tosylate (2 mmol) was also present. The total yield of products obtained was less than 2%.

COMPARATIVE EXPERIMENT B

An experiment was carried out which differed from Example 2 only in that cupric chloride (2 mmol) was also present and that the reaction mixture was kept for 5 h at 65° C. The yields of dimethyl maleate and dimethyl fumarate were only 11% and 1.4%, respectively. No other products had been observed.

We claim as our invention:

1. A process for the preparation of a diester of a 2-butenedioic acid which process comprises reacting at a temperature in the range of from 20° C. to 200° C. and a pressure in the range of from 1 bar to 200 bar an acetylenically unsaturated hydrocarbon having two carbon atoms per molecule less than said 2-butenedioic acid, carbon monoxide, an alcohol and a quinone in the presence of a noble metal selected from the group consisting of Group VIII of the Periodic Table of the Elements and compounds thereof.

2. The process of claim 1 wherein said acetylenically unsaturated hydrocarbon is selected from the group consisting of substituted acetylenically unsaturated hydrocarbons and unsubstituted acetylenically unsaturated hydrocarbons.

3. The process of claim 2 wherein said process is carried out in the presence of palladium and/or a compound of palladium.

4. The process of claim 2 wherein said process is carried out in the presence of a palladium compound.

5. The process of claim 4 wherein said palladium compound is a Pd(II) salt of an alkanoic acid having not more than 12 carbon atoms per molecule.

6. The process of claim 5 wherein said palladium compound(II) is palladium(II) acetate.

7. The process of claim 2 wherein the quinone is a benzoquinone selected from the group consisting of substituted benzoquinone and unsubstituted benzoquinone.

8. The process of claim 7 wherein the benzoquinone is a p-benzoquinone.

9. The process of claim 8 wherein the p-benzoquinone is a halogen-substituted p-benzoquinone.

10. The process of claim 9 wherein the p-benzoquinone is tetrachloro-p-benzoquinone.

11. The process of claim 2 wherein said process is carried out in the presence of a redox agent comprising a methanesulfonate of a compound selected from the group consisting of copper, iron, vanadium, cobalt, and manganese.

12. The process of claim 11 wherein said process is carried out in the presence of a halomethanesulfonate selected from the group consisting of copper, iron, vanadium, cobalt and manganese.

13. The process of claim 12 wherein the halomethanesulfonate is a trihalomethanesulfonate.

14. The process of claim 13 wherein the trihalomethanesulfonate is cupric trifluoromethanesulfonate.

15. The process of claim 2 wherein said process is carried out in the presence of a redox agent comprising a sulfate of a compound selected from the group consisting of copper, iron, vanadium, cobalt and manganese.

16. The process of claim 2 wherein said process is carried out in the presence of a redox agent comprising a perchlorate of a compound selected from the group consisting of copper, iron, vanadium, cobalt and manganese.

17. The process of claim 16 wherein said perchlorate is cupric perchlorate.

18. The process of claim 16 wherein said perchlorate is ferrous perchlorate.

19. The process of claim 2 wherein a molar ratio noble metal of Group VIII and/or a compound thereof to acetylenically unsaturated hydrocarbon in the range of from $10^{-2}$ to $10^{-6}$ is used.

20. The process of claim 15 wherein a molar ratio redox agent to noble metal of Group VIII and/or a compound thereof in the range of from 1 to 200 is used.

21. The process of claim 2 wherein a molar ratio carbon monoxide to acetylenically unsaturated hydrocarbon in the range of from 0.5:1 to 10:1 is applied.

22. The process of claim 2 wherein a molar ratio quinone to acetylenically unsaturated hydrocarbon in the range of from 0.5:1 to 20:1 is applied.

23. The process of claim 2 wherein said process is carried out in the presence of a solvent.

24. The process of claim 23 wherein the solvent comprises an ether.

25. The process of claim 1 wherein the acetylenically unsaturated hydrocarbon is an alkyne having in the range of from 2 to 20 carbon atoms per molecule.

26. The process of claim 25 wherein the acetylenically unsaturated hydrocarbon is an alkyne having in the range of from 2 to 10 carbon atoms per molecule.

27. The process of claim 26 wherein ethyne is used as the starting acetylenically unsaturated hydrocarbon.

28. The process of claim 2 wherein the alcohol is monohydric and has in the range of from 1 to 20 carbon atoms per molecule.

29. The process of claim 28 wherein the alcohol is an alkanol.

30. The process of claim 29 wherein the alkanol is methanol.

* * * * *